United States Patent
Iwasaki et al.

(10) Patent No.: US 7,345,289 B2
(45) Date of Patent: Mar. 18, 2008

(54) SAMPLE SUPPORT PREPARED BY SEMICONDUCTOR SILICON PROCESS TECHNIQUE

(75) Inventors: Kouji Iwasaki, Chiba (JP); Masanso Munekane, Chiba (JP)

(73) Assignee: SII NanoTechnology Inc. (JP)

( * ) Notice: Subject to any disclaimer, the term of this patent is extended or adjusted under 35 U.S.C. 154(b) by 190 days.

(21) Appl. No.: 11/356,698

(22) Filed: Feb. 17, 2006

(65) Prior Publication Data
US 2006/0189021 A1   Aug. 24, 2006

(30) Foreign Application Priority Data
Feb. 21, 2005   (JP) .............................. 2005-044604

(51) Int. Cl.
*H01L 21/00* (2006.01)
*H01J 37/305* (2006.01)
*G01N 1/28* (2006.01)

(52) U.S. Cl. ............... 250/440.11; 250/311; 250/492.2; 250/491.1; 216/2; 438/48
(58) Field of Classification Search ...................... None
See application file for complete search history.

(56) References Cited

U.S. PATENT DOCUMENTS 7,195,872 B2 *   3/2007   Agrawal et al. ................ 435/6
2006/0243655 A1 *   11/2006   Striemer et al. ............ 210/490

* cited by examiner

*Primary Examiner*—Nikita Wells
(74) *Attorney, Agent, or Firm*—Adams & Wilks (57) ABSTRACT

A sample support of the present invention is prepared such that a silicon substrate is used as a raw material, the thickness structure having a shape and a thickness of 10 μm or less is prepared using a semiconductor silicon process technique. The sample support of the present invention is adhered to a partially-cut mesh in a state that a sample portion is not adhered. Further, a plurality of portions where the samples are mounted is arranged on the same substrate.

7 Claims, 6 Drawing Sheets

SAMPLE SUPPORT PREPARED BY SEMICONDUCTOR SILICON PROCESS TECHNIQUE

BACKGROUND OF THE INVENTION

The present invention relates to a sample support which fixes a minute sample such as a TEM viewing sample which is pinpoint-sampled and facilitates additional forming.

Conventionally, with respect to a technique for performing a pinpoint sampling which cuts out a minute sample piece from a specific portion of a sample using a focusing ion beam (FIB) device and for fixing the sample piece to a sample support, various types have been proposed. For example, there have been proposed 1) a method in which a portion of a wafer containing a specified part is mechanically cut out into a block shape and the block is sliced by FIB forming, 2) a method in which holes are formed in portions in front of and behind a specified portion of the wafer by FIB, the thin-piece finish forming is applied to the wafer by FIB, and formed samples are transferred to a mesh and are fixed to the mesh (a lift-out method, see patent document 1), 3) a method in which holes are formed in portions in front of and behind a specified portion of the wafer by FIB and, then, samples in a form of a minute block are picked up and are fixed to a sample support and, thereafter, are subjected to the thin-piece finish forming by FIB (see patent document 2). Since the sample is formed by dicing in the method 1), drawbacks such as the occurrence of cracks and chipping arise and even when the expertise is available, the thickness obtained by thickness forming is limited to 10 μm. With respect to the method 2), the sample piece is ultra-fine and hence, once the sample piece is lost, it is impossible to recover the sample piece and, at the same time, reforming after the pickup operation is impossible. The method 3) which picks up the sample piece in the form of the fine block necessitates a cumbersome operation which requires an expertise. That is, in the method 3), the sample piece is picked up in a fine block form, the fine block is once fixed to a distal end of a probe which is manipulated by a micro manipulator by a FIBCVD, is transferred to a sample support and, thereafter, is separated by cutting.

Figure 7:
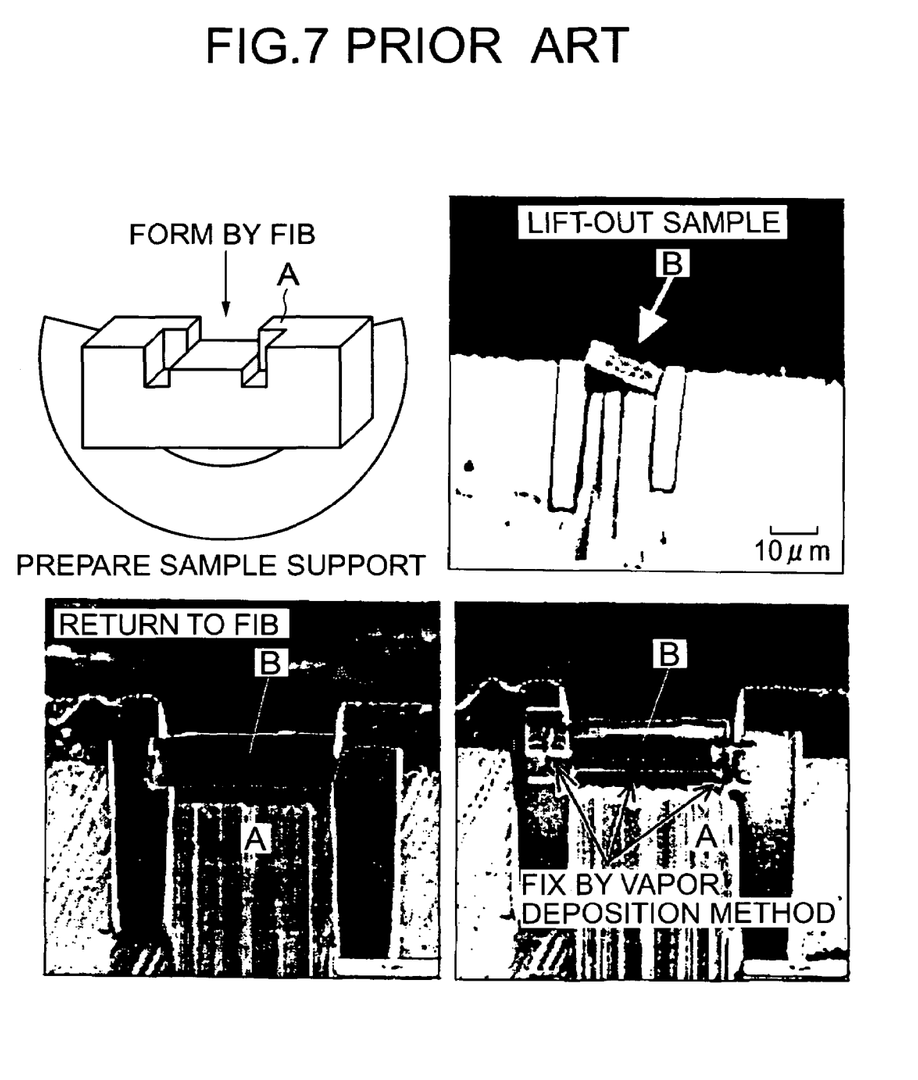
FIG. 7 is a view for explaining a conventional lift-out method which can perform the additional forming.

In non-patent document 1, a method 3) which can perform reforming is disclosed. The method 3) prepares the sample as follows. Since the method 2) which adheres the lift-out sample to the carbon mesh cannot perform the reforming, first of all, a sample support which replaces the mesh is prepared. That is, a Si wafer is polished until a thickness of the Si wafer becomes close to 10 μm by dicing and, thereafter, grooves which prevent the Si wafer from becoming an obstacle in the transmission of electrons at the time of performing the TEM observation and a wall for hanging the lift-out sample are formed in the Si wafer by FIB thus forming a sample support a shown in a left upper portion of FIG. 7. Although the steps until the sample is lifted out is similar to corresponding steps of the lift-out method, it is necessary to perform additional forming after the lift-out step and hence, the FIB forming applied to the sample is temporarily finished while leaving an observation portion having a thickness of 2 to 3 μm. A fine sample piece opening (observation portion) is lifted out from the FIB forming portion by manipulating a micro-manipulator and the fine sample piece opening is hung from the above-mentioned sample support a which is prepared from the Si wafer (a state shown in a right upper portion of FIG. 7). The fine sample piece opening which is placed on the sample support a is again returned to the FIB forming part together with the sample support (a state shown in a left lower portion of FIG. 7), and both ends and a bottom of the sample b are fixed to the sample support b by the FIB deposition using tungsten or the like (a state shown in a right lower portion of FIG. 7). When the sample piece opening is fixed, the reforming for thinning is applied to the sample again.

In applying the additional forming to the sample obtained by the pinpoint sampling, there have been proposed ideas such as the large-sizing of the sample support for lowering a background of the sample support such as mesh, the reduction of thickness of the mesh for reducing a forming portion, and the reduction of a thickness of a portion on which the sample is placed by preparing the sample support by dicing. However, when the thickness of the mesh is reduced, the handling of the mesh becomes difficult and the mesh decreases strength and hence, the mesh is readily bent. Further, a surface of the mesh formed by etching is not uniform and includes waviness and irregularities and hence, the mesh is not suitable for fixing the minute small piece vertically. Further, when the sample support is prepared by forming the Si wafer by dicing, it is possible to prepare the high-quality sample support. However, the dicing is performed manually and hence, the dicing requires the expertise whereby there has been a drawback that it is difficult to manufacture the sample supports on a mass production basis thus pushing up a cost. Further, the dicing forming is liable to cause chipping (cracks and chipping) and hence, it is difficult to set a width of the sample fixing surface to 10 μm or less even with maximum efforts and hence, the width of the sample fixing surface is set to approximately 20 μm. In preparing the TEM sample, to lower the background of the sample support, the sample support is also etched and hence, when the sample support is thick, there has been a drawback that the forming time is prolonged corresponding to the thickness.

[Patent document 1] JP-A-2001-141620 "Cut forming method of sample for transmission electronic microscope" which was laid open on May 25, 2001

[Patent document 2] JP-A-2003-35682 "Sample holder and sample analyzing method" which was laid open on Feb. 7, 2003

[Non-patent document 1] Daisuke Sakata, "FIB lift-out method which enables additional forming" "Written Summary of Lectures presented in the 58th Meeting of Japan Electronic Microscope Society", page 247, May 14 to 16, 2002, Japan Electronic Microscope Society"

The task to be solved by the present invention is to provide a sample support which can perform additional forming of a sample without giving rise to a drawback on flatness of a surface of a mesh, for example, and on the generation of background noises and can fix a thinned sample without requiring an expertise in preparing the sample.

SUMMARY OF THE INVENTION

The sample support of the present invention prepares the thickness structure having a two-dimensional shape and a thickness of 10 μm or less using a silicon substrate as a raw material by a semiconductor silicon process technique.

Further, the two-dimensional shape thickness structure is formed into a terraced configuration and a sample fixing portion is formed on an uppermost stage of a terrace.

Further, the sample support of the present invention is adhered to a partially-cut mesh in a state that a sample portion is not applied to the mesh.

Further, in the sample support of the present invention, a plurality of portions on which the samples are mounted is arranged on the same substrate.

The sample support of the present invention prepares the thickness structure having the thickness of 10 µm or less using the silicon substrate as the raw material by the semiconductor silicon process technique (MEMS: Micro Electro Mechanical Systems) and hence, it is possible to obtain the flatness with the accuracy of sub-micron level on a sample fixing surface without requiring an expertise and, at the same time, it is possible to perform the forming while restricting a width of a sample fixing surface to approximately 5 µm. Since a size of the sample support per se can be reduced by forming, it is possible to prepare a TEM sample with a small background attributed to the scattering of irradiated electrons. This implies that the forming for reducing the thickness of the sample support per se for reducing the background noises conventionally becomes unnecessary thus shortening the forming time. Further, since a large number of sample supports can be prepared at a time, the shortening of the forming time per one piece can be realized whereby the sample supports of high quality can be supplied at a low cost.

Further, since the sample support of the present invention is a support which is fixed to a sample fixing surface in a state that the respective sample pieces are mounted on the sample support in an erected manner, it is possible to perform the additional forming even after the fixing of the sample as well as after the observation.

Further, the shape of the sample support of the present invention adopts the terraced configuration and the sample fixing portion is formed on the uppermost stage of the terrace and hence, it is possible to easily form the sample support by narrowing regions to be etched of the silicon substrate in a step-like manner.

Further, in the sample support of the present invention, the sample support is adhered to the partially-cut mesh in a state that the sample portion is not applied to the mesh. Accordingly, even when the sample support per se is fine, the sample support can be handled easily and, at the same time, since the mesh is not present in the sample piece portion, background noises are not generated.

Further, in the sample support of the present invention, the plurality of portions on which the samples are mounted is arranged on the same substrate and hence, it is possible to place a series of relevant samples on one sample support whereby an experiment such as a comparison observation or the like can be easily performed within a short time and the sample support can be conveniently utilized in the inventory or the quality control of samples. Further, even at the time of performing the additional forming, since the plurality of sample pieces are fixed to one sample support, it is possible to form the plurality of samples sequentially while maintaining environmental conditions inside a chamber such as a vacuum state whereby the forming time can be shortened.

DESCRIPTION OF REFERENCE NUMERALS AND SIGNS

1: silicon substrate
11: single silicon layer
12: base layer
2: mask film
3: resist film
31: developed resist film
4: MEMS sample support
5: mesh

DETAILED DESCRIPTION OF THE INVENTION

Figure 1:
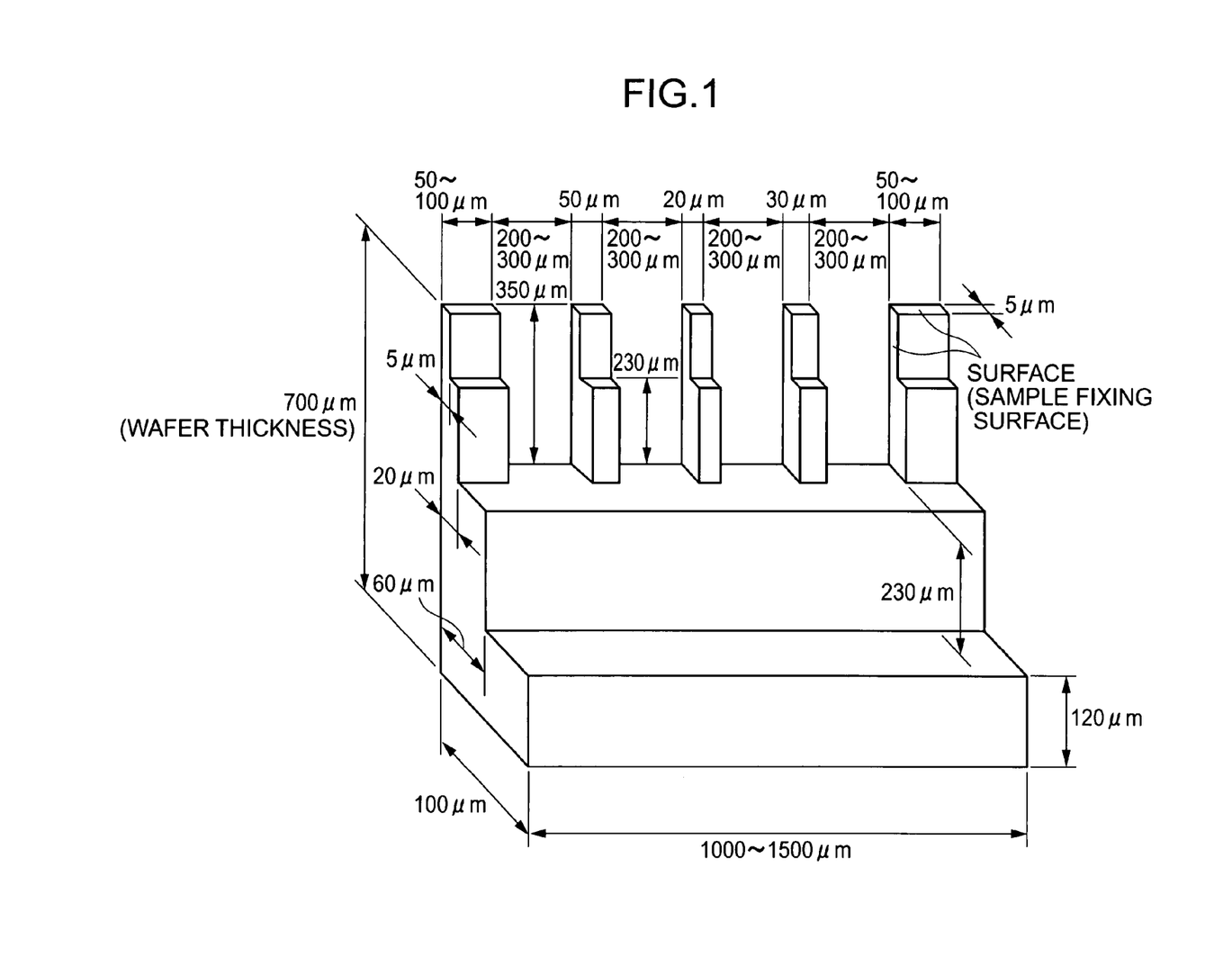
FIG. 1 is a view showing a sample support prepared by a MEMS of the present invention.
Figure 2:
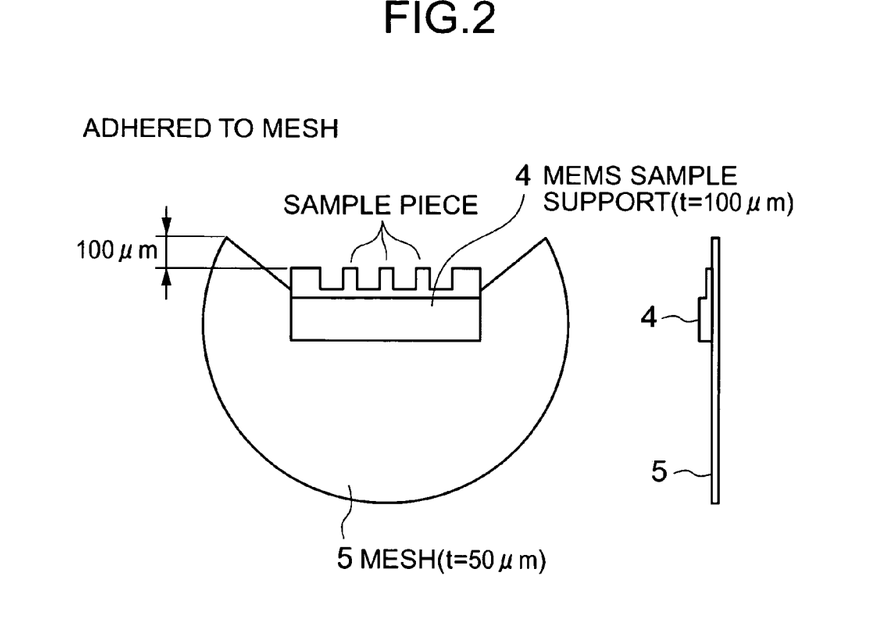
FIG. 2 is a view for explaining a mode in which a sample support is adhered to a mesh.

According to the present invention, using a silicon wafer having a thickness of 100 to 120 µm as a raw material, a sample support is formed by a semiconductor silicon process technique. The general structure of the sample support of the present invention has a terraced shape as shown in FIG. 1, wherein an uppermost stage of the terrace constitutes a sample fixing surface. The terraced shape is formed by a lithography method in the thickness direction of the silicon wafer. That is, 1) a resist film is formed on a surface of the silicon wafer, 2) a protective film is formed by subjecting regions where a current thickness is to be maintained to exposure using a mask pattern, and 3) the resist film is removed and, at the same time, silicon in regions where the protective film is not formed is etched to a desired thickness. 4) A resist film is again formed on the surface of the wafer, 5) a protective film is formed by subjecting regions where a current thickness is to be maintained to exposure using a mask pattern, and 6) the resist film is removed and, at the same time, silicon in regions where the protective film is not formed is etched to a desired thickness. Thereafter, necessary etching is additionally conducted thus forming the wafer until the uppermost stage which constitutes the sample fixing surface has a thickness of 10 µm or less. A size of one sample support is set such that a longitudinal size is 1000 µm or less and a lateral size is 1000 µm to 1500 µm. The sample support is, as shown in FIG. 2, adhered and fixed to a mesh having a diameter of 3 mm and a thickness of approximately 50 µm. The mesh used in this embodiment does not have a full circular shape but is a partially-cut mesh in which a sample fixing portion is notched. This provision is made to prevent the transmission electrons from becoming background noises via the mesh at the time of performing the TEM observation. A surface accuracy of the sample support formed by such a technique is 0.1 µm or less and a surface roughness of the sample support is also ±0.1 µm or less. On the other hand, a surface accuracy of a sample support formed by conventional dicing is several to several tens µm or less and a surface roughness of such a sample support is approximately several µm or less. Here, sizes in the drawing are not numerical values which limit the present invention and are illustrated for allowing those who are skilled in the art to grasp the sizes in general.

EMBODIMENT 1

Figure 3:
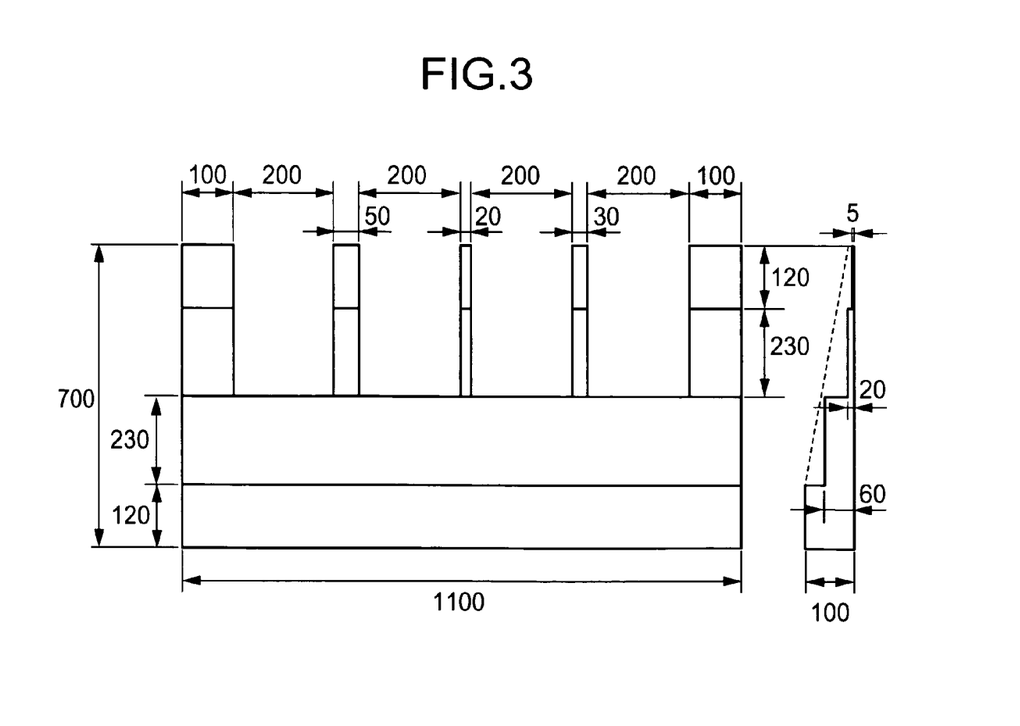
FIG. 3 is a view showing an embodiment of a sample support prepared by a MEMS of the present invention.
Figure 4A:
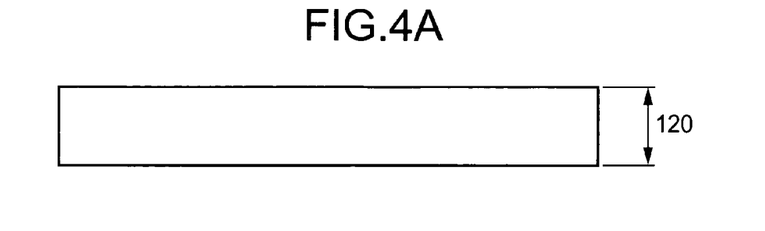
FIGS. 4A-4D are views for explaining a mask pattern used at the time of preparing the sample support of the embodiment.
Figure 5A:
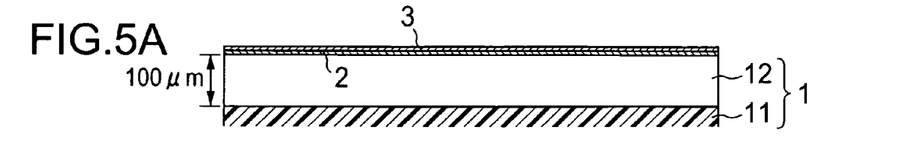
FIGS. 5A-5K are views for explaining a process for preparing the sample support of the embodiment.
Figure 5B:
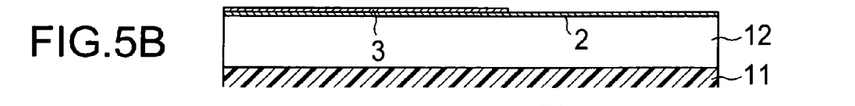
Figure 5C:
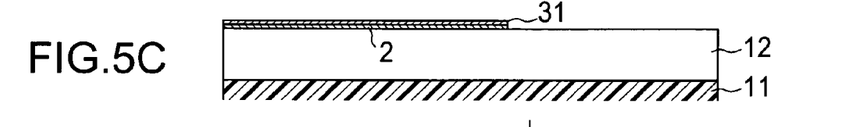
Figure 5D:
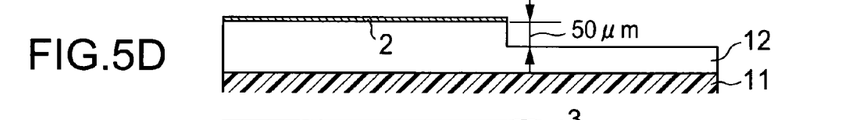

The manufacturing steps of one embodiment of the sample support according to the present invention shown in FIG. 3 are explained in conjunction with FIGS. 4A-4D and FIGS. 5A-5J. A silicon substrate 1 which forms a single silicon layer 12 having a thickness of 100 μm on a base layer 11 is used as a raw material. A mask film 2 is formed on a surface of the single silicon layer 12 of the silicon substrate 1 as shown in FIG. 5A, and a resist film 3 for lithography is formed on the mask film 2. Next, a mask for lithography is prepared for forming a front surface of a lowermost stage of a terrace into a longitudinal size of 400 μm and a lateral size of 1100 μm. A shape of the mask conforms to a shape shown in FIG. 4A. As a matter of course, the number of mask patterns is not limited to one and a large number of mask patterns corresponding to the number of sample supports which can be formed on the wafer are arranged in a matrix array. The pattern of the mask is transferred to the above-mentioned resist film 3 by the irradiation of ultraviolet rays. Due to such steps, as shown in FIG. 5B, a region corresponding to a front surface portion of the lowermost stage of the terrace is covered with a resist 31 on the mask film 2, while the mask film 2 is exposed at other portions. When the mask film 2 is etched in such a state, as shown in FIG. 5C, the silicon layer 12 is exposed at portions except for the region which is covered with the resist 31. Then, a resist peel-off liquid is injected to the resist 31 to remove the resist 31. Subsequently, anisotropic etching is applied to the silicon layer 12 in the direction perpendicular to the surface until an etching depth reaches 50 μm. Due to such steps, a lowermost terraced surface having a width of 50 μm is formed as shown in FIG. 5D.

Figure 4B:
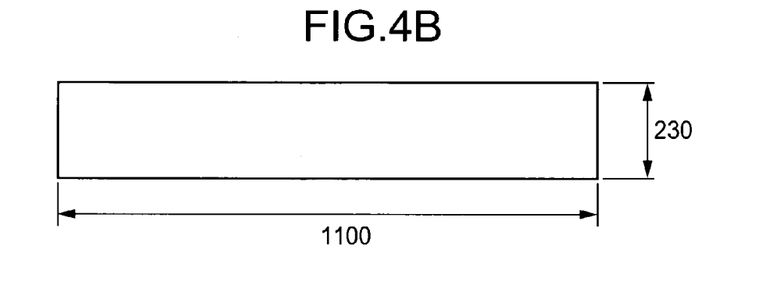
Figure 4C:
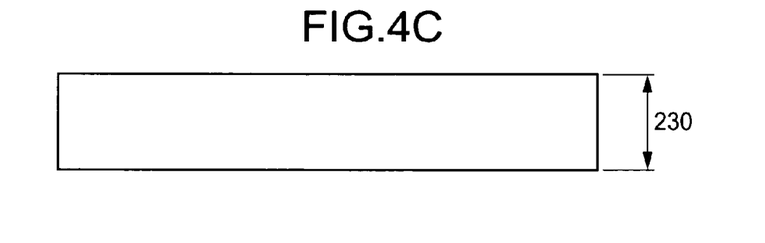
Figure 5E:
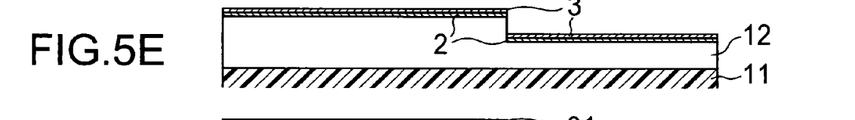
Figure 5F:
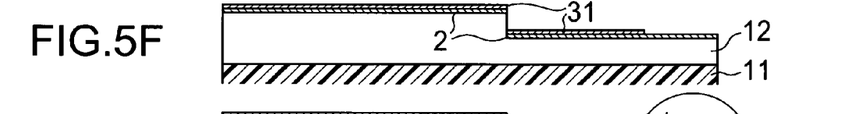

Subsequently, as shown in FIG. 5E, on the surface of the substrate, a mask film 2 is formed and a resist film 3 is formed on the mask film 2 again. This time, a mask for lithography is prepared for forming a front surface of a second stage of the terrace into a longitudinal size of 180 μm and a lateral size of 1100 μm, and a pattern of the mask is transferred to the above-mentioned resist film 3 by the irradiation of ultraviolet rays. A shape (A+B) of the mask is formed by adding a shape shown in FIG. 4B to the preceding shape shown in FIG. 4A. Due to such steps, as shown in FIG. 5F, regions corresponding to the front surface portion of the first stage of the terrace and the front surface portion of the second stage of the terrace are covered with a resist 31 on the mask film 2, while the mask film 2 is exposed at other portions. When the mask film 2 is etched in such a state, the silicon layer 12 is exposed at portions except for the region which is covered with the resist 31. Then, the resist 31 is removed and anisotropic etching is applied to the silicon layer 12 in the direction perpendicular to the surface until an etching depth reaches 30 μm. Due to such steps, a second terraced surface is formed as shown in FIG. 5G.

Figures 5G, 5H:
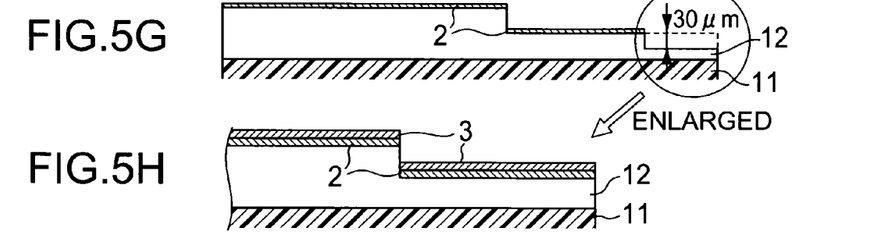
Figures 5I, 5J, 5K:
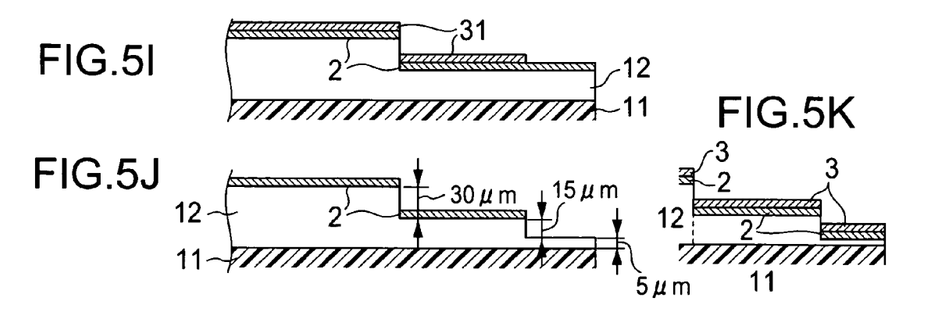

Subsequently, as shown in FIG. 5H in a partially enlarged manner, on the surface of the substrate, a mask film 2 is formed and a resist film 3 is formed on the mask film 2 thirdly. This time, a mask for lithography is prepared for forming a third stage of the terrace. A shape of the mask is, as shown in C in FIG. 4, a shape (A+B+C) formed by adding a rectangular pattern of a longitudinal size of 90 μm and a lateral size of 1100 μm to the preceding mask shape, and a pattern of the mask is transferred to the above-mentioned resist film 3 by the irradiation of ultraviolet rays. Due to such steps, as shown in FIG. 5I, a region corresponding to the front surface portions of the first to third stages of the terrace is covered with a resist 31 on the mask film 2, while the mask film 2 is exposed at other portions. When the mask film 2 is etched in such a state, the silicon layer 12 is exposed at portions except for the region which is covered with the resist 31. Then, the resist 31 is removed and anisotropic etching is applied to the silicon layer 12 in the direction perpendicular to the surface until an etching depth reaches 15 μm. Due to such steps, a third terraced surface and the uppermost terraced surface are formed as shown in FIG. 5J.

Figure 4D:
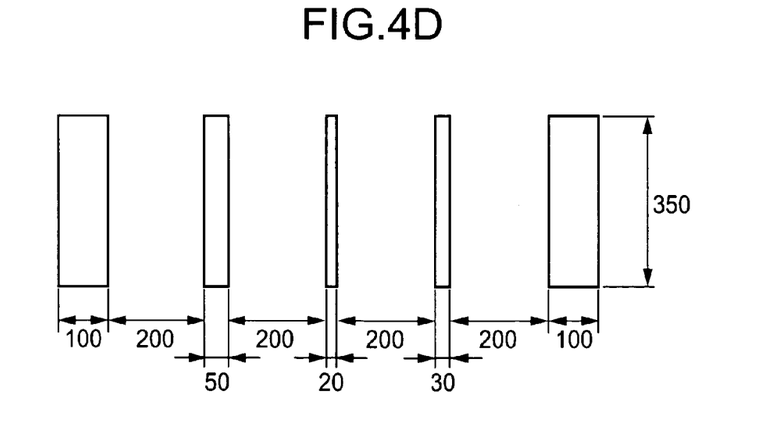

Subsequently, as shown in FIG. 5K, on the surface of the substrate, a mask film 2 is formed and a resist film 3 is formed on the mask film 2 fourthly. This time, a mask for lithography is prepared for forming a sample fixing portion which constitutes an uppermost stage of the terrace in a separated manner. A shape of the mask is, as shown in FIG. 4D, since the uppermost stage and the third terraced stage portion are separated from each other in this embodiment, to conform with a height of 120 μm of both stages, a shape (A+B+D) formed by adding five rectangular patterns consisting of a pattern having a longitudinal size of 120 μm and a lateral size of 1100 μm, a pattern having a longitudinal size of 120 μm and a lateral size of 50 μm which is arranged in a spaced-apart manner in the laterally direction with a distance of 200 μm, a pattern having a longitudinal size of 120 μm and a lateral size of 20 μm which is arranged in a spaced-apart manner in the laterally direction with a distance of 200 μm, a pattern having a longitudinal size of 120 μm and a lateral size of 30 μm which is arranged in a spaced-apart manner in the laterally direction with a distance of 200 μm, and a pattern having a longitudinal size of 120 μm and a lateral size of 100 μm which is arranged in a spaced-apart manner in the laterally direction with a distance of 200 μm to the patterns A and B, and the patterns of the mask are transferred to the above-mentioned resist film 3 by the irradiation of ultraviolet rays. Due to such steps, the mask film 2 is exposed in a state that only regions which constitute front surface portions of the third stage and the uppermost stage of the terrace and are separated are not covered with a resist 31 on the mask film 2. When the mask film 2 is etched in such a state, the silicon layer 12 is exposed at portions which are not covered with the resist 31. Subsequently, anisotropic etching is applied to the silicon layer 12 in the direction perpendicular to the surface until the silicon layer 12 is eliminated and the base layer 11 is exposed. Here, the portions to be etched form a right-side portion from a broken line shown in FIG. 5K. Due to such forming, the third stage and the uppermost stage of the terrace are split in five.

Upon completion of the silicon forming step along with the above-mentioned process, the resist is removed using a resist peel-off liquid and, subsequently, the mask film 2 is removed. In this manner, a large number of silicon sample supports according to this embodiment are formed on the base layer 11 of the substrate 11.

In this manner, according to the present invention, the sample support 4 is prepared using the MEMS technique and hence, it is possible to form the extremely thin sample fixing surface. The surface accuracy is ±1 μm or less and the surface roughness is also 0.1 μm or less. The sample support 4 is adhered to the partially-cut circular mesh 5 having a thickness of approximately 50 μm and a diameter of approximately 3 mm using a conductive adhesive agent as shown in FIG. 2. The conductive adhesive agent is used for preventing the sample from electrically floating attributed to the storing of charge by the irradiation of charged particles. In place of the conductive adhesive material, it is possible to adopt a treatment which applies conductive coating.

Figure 6:
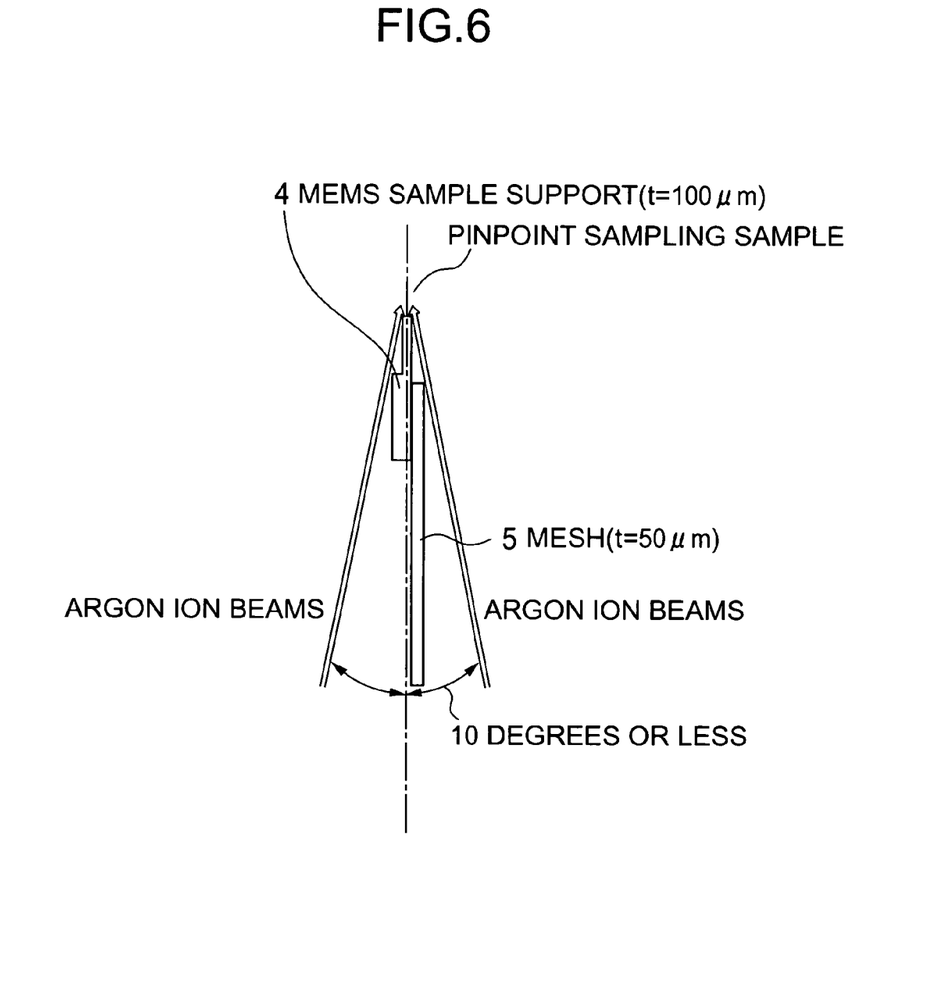
FIG. 6 is an explanatory view showing that a thickness of the sample support allows the irradiation of Ar ion beams from below.

A minute sample piece which is obtained by pinpoint sampling is fixed to an uppermost stage of the terrace. For example, the minute sample piece is fixed to the sample support of the present invention and, thereafter, in case of the sample for TEM observation, the thinning forming is performed by the FIB using Ga ions. In such forming, there arise drawbacks such as the ion retention. To cope with such drawbacks, the finishing forming which removes residual Ga ions generated in the FIB using Ar ions is performed. In such processing, since the sample support of the present invention can be prepared with an extremely small thickness, this forming can be performed by the irradiation of ions from below as shown in FIG. 6. That is, provided that an angle made by the Argon beams and the mesh 5 is 10 degrees or less, even when the sample support is present, it is possible to perform the irradiation of Ar ion beams to the sample and hence, the irradiation of beams can be performed from such a direction whereby there exists substantially no possibility of re-adhesion of Ga ions.

Although the sample support of the present invention has been explained heretofore using the pinpoint sampling for TEM observation as an example, the present invention is not limited to such observation and is broadly applicable to a DEM sample or minute samples used for other surface analyzer.

What is claimed is:

1. A sample support in which the thickness structure having a two-dimensional shape and a thickness of 10 µm or less is prepared using a silicon substrate as a raw material by a semiconductor silicon process technique.

2. A sample support according to claim 1, wherein the thickness structure having the two-dimensional shape is formed into a terraced configuration and a sample fixing portion is formed on an uppermost stage of a terrace.

3. A sample support according to claim 2, wherein the sample support is adhered to a partially-cut mesh in a state that a sample portion is not applied to the mesh.

4. A sample support according to claim 3, wherein a plurality of portions on which the samples are mounted are arranged on the same substrate.

5. A sample support according to claim 2, wherein a plurality of portions on which the samples are mounted are arranged on the same substrate.

6. A sample support according to claim 1, wherein the sample support is adhered to a partially-cut mesh in a state that a sample portion is not applied to the mesh.

7. A sample support according to claim 1, wherein a plurality of portions on which the samples are mounted are arranged on the same substrate.

* * * * *